United States Patent
Fischer et al.

(10) Patent No.: US 7,137,814 B2
(45) Date of Patent: Nov. 21, 2006

(54) DENTAL TREATMENT TRAY COMPRISING A PLASTICIZED RESIN FOR IMPROVED MOLDABILITY AND CONFORMABILITY

(75) Inventors: Dan E. Fischer, Sandy, UT (US); Derrick P. Christman, South Weber, UT (US)

(73) Assignee: Ultradent Products, Inc., South Jordan, UT (US)

(*) Notice: Subject to any disclaimer, the term of this patent is extended or adjusted under 35 U.S.C. 154(b) by 129 days.

(21) Appl. No.: 10/962,884

(22) Filed: Oct. 12, 2004

(65) Prior Publication Data
US 2006/0078848 A1    Apr. 13, 2006

(51) Int. Cl.
*A61C 17/02* (2006.01)
*A61C 5/00* (2006.01)

(52) U.S. Cl. .......................... 433/80; 433/80; 433/215
(58) Field of Classification Search ............. 433/215, 433/83, 80, 6
See application file for complete search history.

(56) References Cited

U.S. PATENT DOCUMENTS

| | | | |
|---|---|---|---|
| 4,204,323 A | 5/1980 | Neubert et al. | 433/38 |
| 4,867,680 A * | 9/1989 | Hare et al. | 433/37 |
| 5,108,286 A * | 4/1992 | Freedman et al. | 433/37 |
| 5,346,395 A | 9/1994 | Adell | 433/71 |
| 5,415,544 A * | 5/1995 | Oxman et al. | 433/48 |
| 5,503,552 A | 4/1996 | Diesso | 433/37 |
| 5,562,449 A | 10/1996 | Jacobs et al. | 433/215 |
| 5,616,027 A | 4/1997 | Jacobs et al. | 433/37 |
| 5,769,633 A | 6/1998 | Jacobs et al. | 433/37 |
| 6,196,840 B1 | 3/2001 | Zentz et al. | 433/71 |
| 6,280,196 B1 * | 8/2001 | Berghash | 433/215 |
| 6,302,690 B1 * | 10/2001 | Brandhorst et al. | 433/45 |
| 6,322,360 B1 | 11/2001 | Burgio | 433/80 |
| 6,582,708 B1 | 6/2003 | Sagel et al. | 424/410 |
| 6,629,841 B1 | 10/2003 | Skinner | 433/43 |
| 6,770,361 B1 * | 8/2004 | Kong | 428/354 |
| 6,964,571 B1 * | 11/2005 | Andersen et al. | 433/215 |
| 2003/0234022 A1 | 12/2003 | Belfer | 128/861 |
| 2004/0002034 A1 | 1/2004 | Jacobs et al. | 433/48 |
| 2004/0038171 A1 | 2/2004 | Jacobs et al. | 433/37 |
| 2004/0038172 A1 | 2/2004 | Jacobs et al. | 433/37 |
| 2004/0038183 A1 | 2/2004 | Jacobs et al. | 433/215 |
| 2004/0146836 A1 | 7/2004 | Anderson | 433/215 |
| 2004/0146837 A1 | 7/2004 | Anderson | 433/215 |
| 2004/0234929 A1 * | 11/2004 | Fischer et al. | 433/215 |

OTHER PUBLICATIONS

"DuPont Industrial Polymers: Elvax Safety in Handling and Use" 1997, http://www.dupont.com/industrial-polymers/elvax/H-24228-1.html.

(Continued)

Primary Examiner—Cary E. O'Connor
(74) Attorney, Agent, or Firm—Work Nydegger

(57) ABSTRACT

A dental treatment tray used to provide a desired treatment is injection molded from a composition that includes at least one thermoplastic resin and at least plasticizer. The plasticized thermoplastic resin permits the dental treatment tray to be injection molded even while having a wall thickness less than about 0.015 inch. The plasticizer increases the melt flow index of the thermoplastic resin while in a molten state, which facilitates complete filling of the mold cavity by the thermoplastic resin. The plasticizer also softens the thermoplastic polymer while in a solidified state in order to yield a dental tray that is even more flexible and comfortable for the user to wear.

28 Claims, 6 Drawing Sheets

OTHER PUBLICATIONS

"DuPont Industrial Polymers: Elvax and Wax—A Good Fit" 1997, http://www.dupont.com/industrial-polymers/elvax/H-49652/H-49652.html.

"DuPont Industrial Polymers: Elvax 750 Product Information" 1997, http://www.dupont.com/industrial-polymers/elvax/E-54510.html.

"DuPont Dow Elastomers: Engage Polyolefin Elastomers, The Critical Ingredient for Success" ENS-H90110-00-A110, 2000.

"DuPont Industrial Polymers: Elvax Grade Selection Guide" 2001, http://www.dupont.com/industrial-polymers/elvax/H-08772-2/H-08772-2.html.

Hi Valley Chemical "Mineral Oil—Material Safety Data Sheet" Effective Nov. 2, 2001, http://www.jtbaker.com/msds/englishhtml/m7700.htm.

"DuPont Material Safety Data Sheet—Engage" ENG002, rev. May 10, 2002.

"DuPont Industrial Polymers: Elvax Injection Molding Guide" Doc. Ref. VAX020424.1v1, rev. May 24, 2002, p. 11.

DuPont Dow Elastomers "Engage 8401" Dec. 2003.

DuPont Dow Elastomers "Engage Typical Properties" Feb. 2004.

"DuPont Industrial Polymers: Thermal Properties of Elvax" 2004, http://www.dupont.com/industrial-polymers/elvax/H-49653-1/H-49653-1.html.

"DuPont Material Safety Data Sheet—Elvax" VAX0001, rev. Jun. 28, 2004.

DuPont Dow Elastomers "Engage—Product Grade Chart" Feb. 2004.

DuPont Dow Elastomers "Engage—Injection Molding Reference Guide" Apr. 2004.

* cited by examiner

DENTAL TREATMENT TRAY COMPRISING A PLASTICIZED RESIN FOR IMPROVED MOLDABILITY AND CONFORMABILITY

BACKGROUND OF THE INVENTION

1. The Field of the Invention

The present invention is in the field of shaped, flexible dental trays used to deliver a dental treatment composition to a person's teeth. More particularly, the invention relates to flexible dental trays that can be injection molded from a thermoplastic polymer mixed with a plasticizer.

2. The Relevant Technology

Virtually all people desire white or whiter teeth. To achieve this goal, people have veneers placed over their teeth or have their teeth chemically bleached. A common bleaching method involves the use of a dental tray that is custom-fitted to a person's teeth and that is therefore comfortable to wear. One type of customized tray is made from a stone cast of a person's teeth. Another is customized directly using a person's teeth as a template (e.g., "boil-and-bite" trays). Non-customized trays that approximate the shapes and sizes of a variety of users' dental arches have also been used. A dental bleaching composition is placed into the tray and the tray placed over the person's teeth for a desired period of time.

Another bleaching method involves painting a bleaching composition directly onto a person's teeth. A perceived advantage of paint-on bleaching is that it eliminates the need for a dental tray. The main disadvantage of a paint-on bleaching composition is that it remains directly exposed to the person's saliva and disruptive forces found in a person's mouth. As a result, a significant portion of the bleaching composition does not remain on the teeth where bleaching is desired. Some or all of the composition can dissolve away into the person's saliva and/or be transferred to adjacent oral tissues, potentially irritating soft oral tissues.

Another tooth bleaching method involves placing a flexible bleaching strip over a user's tooth surfaces. Conventional bleaching strips comprise a flexible plastic strip coated with a dental bleaching gel of moderate viscosity and relatively low stickiness on the side of the strip facing the user's teeth. To install the bleaching strip, a portion of the bleaching strip is placed over the front surfaces of the user's teeth, and the remainder is folded around the occlusal edges of the teeth and against a portion of the lingual surfaces. Like paint-on bleaching compositions, this procedure does not require the use of dental trays. Unlike paint-on bleaching compositions, bleaching strips include a plastic barrier that, at least in theory, keeps the dental bleaching gel from diffusing into the user's mouth.

In reality, because of the generally poor adhesion of bleaching strips to the user's teeth, coupled with their generally flimsy nature, it is often difficult for the user to maintain the bleaching strip in its proper position for the recommended time. Even if a user successfully maintains a conventional bleaching strip in its proper position during the recommended bleaching period, the bleaching gel often diffuses into the person's saliva, potentially causing a poor taste in the user's mouth and possibly discomfort to soft oral and throat tissues. The tendency of the bleaching gel to diffuse into the user's mouth can be accelerated through even minimal shifts of the bleaching strip over the user's teeth, with each shift potentially causing bleaching gel that remains adhered to the user's teeth, but not covered by the plastic strip, to be exposed to saliva in the user's mouth. In some cases, the bleaching strip can become so dislodged or mangled that it must be removed by the user and replaced with a fresh bleaching strip to complete the recommended bleaching time. This multiplies the cost and hassle of using conventional bleaching strips.

Ultimately, the main impediment to successful bleaching is the failure of users to complete the prescribed bleaching regimen. If the bleaching apparatus is difficult to install over a person's teeth, requires numerous repetitions to achieve observable results, or is uncomfortable to wear, the user may simply give up and prematurely abort the prescribed bleaching regimen. Thus, even if dental bleaching is possible using a particular bleaching apparatus or method, it is less likely to occur if the inadequacies of the bleaching apparatus or method cause a user to become discouraged before desired results are attained.

The thickness of a dental tray is often an important characteristic in determining the resulting comfort of the tray. Thinner trays provide increased flexibility and conformability. The manufacture of thin-walled trays by vacuum forming a polymer sheet is more expensive and time consuming than injection molding. Whereas injection molding is a viable process for manufacturing thicker-walled trays and mouth guards, it has heretofore not been possible to injection mold trays thinner than about 0.015 inch. As a result, trays having a thickness less than 0.015 inch must still be vacuum formed from an initially flat sheet.

It would be an improvement in the art to provide improved thermoplastic compositions that permit dental trays having thicknesses less than about 0.015 to be injection molded while having sufficient flexural strength to resist collapse after being demolded. Such an improvement would provide a low cost, high quality dental tray with increased flexibility and conformability, which would be expected to improve or encourage compliance to a treatment regimen by the user.

BRIEF SUMMARY OF THE PREFFERED EMBODIMENTS

The present invention generally relates to improved dental treatment trays used to deliver a dental treatment composition (e.g., a dental bleaching composition) to a person's teeth. The inventive dental treatment trays are formed from a thermoplastic resin and a plasticizer selected and included in an amount so as to permit the tray to be injection molded while having a thickness less than about 0.015 inch. The reduced thickness, as well as the plasticizer, yield a dental tray that is very soft, flexible and able to conform to a person's teeth, but not so flimsy as to lose their ability to retain the shape of a tray. The dental trays according to the invention, by virtue of their high flexibility, are able to fit a variety of differently-sized and shaped teeth, eliminating the need to provide a custom-fitted tray formed from a stone model of a person's teeth.

Examples of thermoplastic resins that can be used to form the dental treatment trays include, but are not limited to, one or more of polyolefins, ethylene-vinyl acetate copolymer (EVA), ethylene-vinyl alcohol copolymer (EVAL), polycaprolactone (PCL), polyvinyl chloride (PVC), polyesters, polycarbonates, polyamides, polyurethanes, and polyesteramides. Examples of suitable polyolefins include, but are not limited to, polyethylene (PE), high density polyethylene (HDPE), low density polyethylene (LDPE), ultra low density polyethylene (ULDPE), and polypropylene (PP).

One or more plasticizers are also included to modify the properties of the thermoplastic resin. In one aspect, the plasticizer imparts increased flowability of the polymer when heated during molding. In another aspect, the plasticizer may also affect the flexibility and conformability of the finished dental tray to the person's teeth during use. Examples of suitable plasticizers include oils (e.g., mineral oil, especially white mineral oil, and paraffin oil), waxes (e.g., paraffin wax), petrolatum, liquid petrolatum, and nujol. In general, preferred plasticizers are hydrophobic to prevent leaching into a user's mouth during use (i.e., hydrophilic plasticizers can more easily diffuse out of the dental tray when exposed to saliva or water).

Plasticizers such as mineral oil, which are liquid at room temperature, increase the melt flow index of the thermoplastic resin while in a molten state, which assists in injection molding dental treatment trays having very thin walls (i.e., less than about 0.015 inch). They also tend to impart a softening effect to the finished dental treatment trays upon cooling and solidification of the thermoplastic resin. Plasticizers such as wax, which are solid at room temperature but liquid while the thermoplastic resin is in a molten state, also increase the melt flow index of the thermoplastic resin while in a molten state but can impart some rigidity to the finished dental treatment tray upon cooling. Providing a mixture of plasticizers that are liquid and solid at room temperature (e.g., mineral oil and paraffin wax) provides excellent moldability of the thermoplastic resin while in a thermoplastic state, as well as a finished dental tray that is softened while able to better maintain the shape of a tray. The term "solid" shall encompass true solids, as well as pastes.

By using a composition comprising a thermoplastic material and a plasticizer, it is possible to form dental trays through injection molding while having very thin cross sections. Because the plasticizer increases the melt flow index of the thermoplastic material, the molten thermoplastic resin is better able to flow into and fill the mold cavity of the injection molding apparatus. This allows the injection molding of dental treatment trays having a thickness less than about 0.015 inch, preferably less than about 0.01 inch, and more preferably less than about 0.005 inch.

According to one embodiment, the dental tray has a tray configuration comprising a front side wall and a bottom wall that form an approximate L-shaped cross section. Alternatively, the tray may include a front side wall, bottom wall and rear side wall that form an approximate U-shaped cross section.

According to one embodiment, the dental treatment trays may be pre-loaded with a dental treatment composition. The treatment composition may comprise a sticky viscous gel, a less viscous gel, a highly viscous putty, or a substantially solid composition that is less adhesive prior to being moistened with saliva or water but that becomes more sticky and adhesive when moistened.

The size and shape of the dental treatment trays according to the invention can be tailored to readily fit a person's upper or lower dental arch. The treatment trays may come in various sizes (e.g., small, medium and large) to better adapt to differently-sized dental arches and/or teeth among the population at large. The dental treatment trays are advantageously designed so as to substantially cover the front and lingual surfaces of the teeth and/or gums to be treated.

According to one embodiment, the treatment trays may be used in combination with a supporting structure, such as an outer support tray, prior to use. An outer support tray is particularly useful when the dental tray is so flexible as to be difficult to place over a person's teeth without collapsing. The outer support tray may have the same configuration as the treatment tray so as to receive and support the treatment tray in a nesting fashion. In one embodiment, the outer support tray includes a handle to facilitate gripping and maneuverability of the outer support tray while placing the treatment tray over the teeth. Once positioned, the outer support tray can be removed so as to leave the treatment tray in place over the teeth.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

Figure 1:
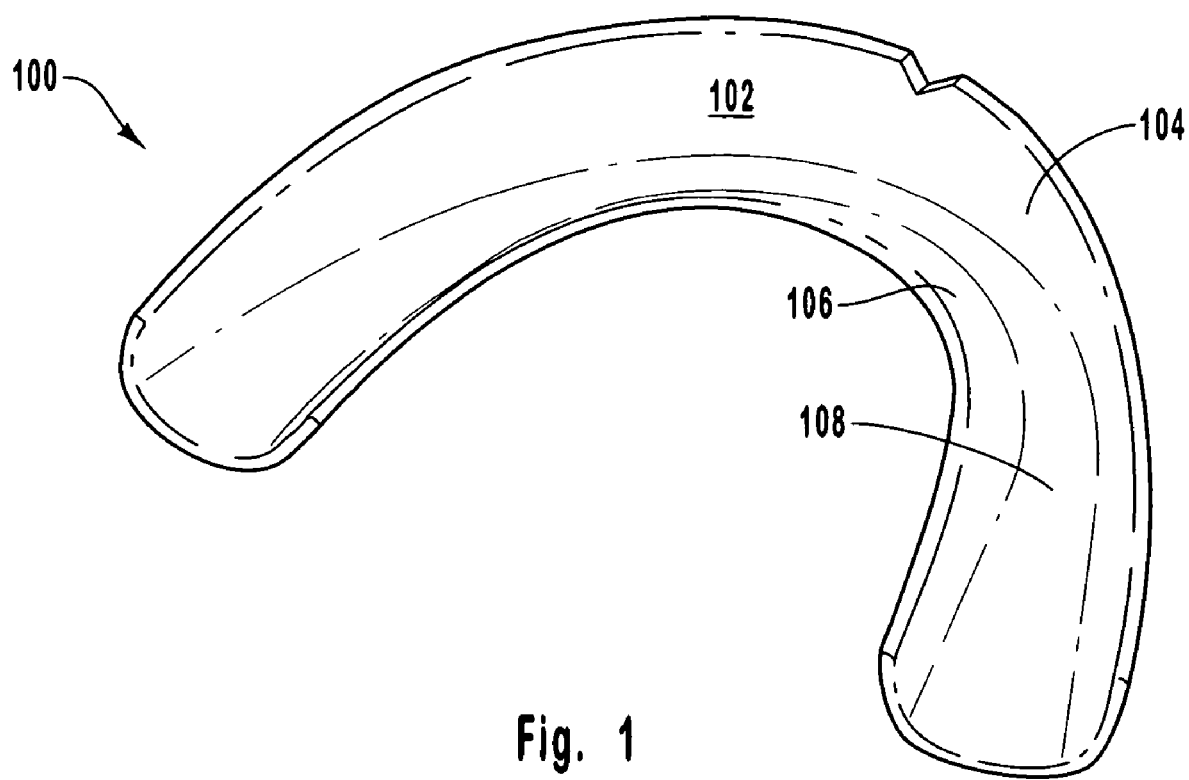
FIG. 1 is a perspective view of an exemplary dental treatment tray according to the invention.

The present invention relates to improved dental treatment trays used to deliver a dental treatment composition to a person's teeth comprising a mixture of a thermoplastic resin and a plasticizer. The combination of the thermoplastic material and plasticizer permits the dental treatment trays to be formed by injection molding while having a thickness less than about 0.015 inch, which was heretofore very difficult, if not impossible. Moreover, adding a plasticizer to the thermoplastic resin yields a dental tray that is significantly softer and more flexible compared to a tray formed from the thermoplastic resin by itself. The high flexibility permits the dental tray to conform to a person's teeth, eliminating the need to provide a custom-fitted tray formed from a stone model of a person's teeth.

The ability to injection mold a thin-walled dental treatment tray is a significant improvement in the art since it is much cheaper and time effective than vacuum forming methods. Moreover, the improved softness of the final tray increases the comfort to the user, which might be expected to increase compliance with a given treatment regimen.

Examples of thermoplastic resins that can be used to form the dental treatment trays include, but are not limited to, one or more of polyolefins, ethylene-vinyl acetate copolymer (EVA), ethylene-vinyl alcohol copolymer (EVAL), polycaprolactone (PCL), polyvinyl chloride (PVC), polyesters, polycarbonates, polyamides, polyurethanes, and polyesteramides. Examples of suitable polyolefins include, but are not limited to, polyethylene (PE), high density polyethylene (HDPE), low density polyethylene (LDPE), ultra low density polyethylene (ULDPE), and polypropylene (PP).

The thermoplastic resin may be included in a broad range of about 10% to about 99% by weight of the dental treatment trays. To better obtain the benefits described herein, the thermoplastic resin is preferably included in an amount in a range of about 25% to about 95% by weight of the dental treatment trays, more preferably in a range of about 40% to about 90% by weight, and most preferably in a range of about 50% to about 80% by weight.

According to one exemplary embodiment, the thermoplastic material may comprise a mixture of an ethylene-octene copolymer (DuPont-Dow Engage 8401) and ethylene vinyl acetate copolymer (e.g., Elvax 750). The ratio of the ethylene-octene copolymer to the ethylene vinyl acetate copolymer is preferably in a range of about 1:20 to about 20:1, more preferably in a range of about 1:10 to about 10:1, and most preferably in a range of about 1:5 to about 5:1.

One or more plasticizers are included to modify and improve the properties of the thermoplastic resin. In one aspect, the plasticizer increases the melt flow index of the thermoplastic polymer when heated during molding. In another aspect, the plasticizer may advantageously improve the flexibility and/or mechanical stability of the finished dental tray.

Examples of suitable plasticizers include oils (e.g., mineral oil, especially white mineral oil, and paraffin oil), waxes (e.g., paraffin wax), petrolatum, liquid petrolatum, and nujol. In general, preferred plasticizers are hydrophobic to prevent leaching into a user's mouth during use (i.e., hydrophilic plasticizers can more easily diffuse out of the dental tray when exposed to saliva or water).

Plasticizers such as mineral oil, which are liquid at room temperature, increase the melt flow index of the thermoplastic resin while in a molten state, which assists in injection molding dental treatment trays having very thin walls (i.e., less than about 0.015 inch). They also tend to impart a softening effect to the finished dental treatment trays upon cooling and solidification of the thermoplastic resin.

Plasticizers such as wax, which are solid at room temperature but liquid while the thermoplastic resin is in a molten state, also increase the melt flow index of the thermoplastic resin while in a molten state but can impart some rigidity to the finished dental treatment tray upon cooling. Providing a mixture of plasticizers that are liquid and solid at room temperature (e.g., mineral oil and paraffin wax) provides excellent moldability of the thermoplastic resin while in a thermoplastic state, as well as a finished dental tray that is softened while able to better maintain the shape and mechanical integrity of a tray.

By using a composition comprising a thermoplastic material and a plasticizer, it is possible to form dental trays through injection molding while having very thin cross sections. Increasing the melt flow index of the thermoplastic material improves the ability of the molten thermoplastic resin to flow into and fill the mold cavity of the injection molding apparatus. This allows the injection molding of dental treatment trays having a thickness less than about 0.015 inch, preferably less than about 0.01 inch, and more preferably less than about 0.005 inch.

The plasticizer may be included in a broad range of about 1% to about 90% by weight of the dental treatment trays. To better obtain the benefits described herein, the plasticizer is preferably included in an amount in a range of about 5% to about 75% by weight of the dental treatment trays, more preferably in a range of about 10% to about 60% by weight, and most preferably in a range of about 20% to about 50% by weight.

Flow additives, fillers, and additional modifiers known in the art may be used as desired to modify the properties of the composition used to form the shaped barrier layer.

The dental treatment tray may be used in combination with an outer support tray. The outer support tray is positioned adjacent to the treatment tray so as to help maintain the tray in a desired configuration prior to and while placing the tray over a person's teeth. The outer support tray may have the same configuration as the shaped barrier layer. The outer support tray may also assist the user in placing the treatment tray over a person's teeth. The outer support tray may include a handle to facilitate gripping and maneuverability of the support tray while placing the treatment tray over the teeth. Once the treatment tray has been placed over the person's teeth, the support tray is removed, leaving only the treatment tray in the user's mouth. The support tray can be formed of any suitable thermoplastic material having sufficient rigidity to support the treatment tray.

According to one embodiment, the dental treatment tray may include one or more dental treatment compositions pre-loaded therein. The treatment composition may comprise a sticky viscous gel, a less viscous gel, a highly viscous putty, or a substantially solid composition that is less adhesive prior to being moistened with saliva or water but that becomes more sticky and adhesive when moistened. The dental treatment composition typically includes at least one tissue adhesion agent and at least one active agent known in the art.

Examples of tissue adhesion agents include, but are not limited to polyvinyl pyrrolidone (PVP), carboxypolymethylene (e.g., CARBOPOL, sold by Novean, Inc.), polyethylene oxide (e.g., POLYOX, made by Union Carbide), polyacrylic acid polymers or copolymers (e.g., PEMULEN, sold by Novean, Inc.), polyacrylates, polyacrylamides, copolymers of polyacrylic acid and polyacrylamide, PVP-vinyl acetate copolymers, carboxymethylcellulose, carboxypropylcellulose, polysaccharide gums, proteins, and the like.

The amount of tissue adhesion agent in the dental treatment composition depends on whether the composition is a gel, a putty, or a substantially solid adhesive composition. According to one embodiment, the tissue adhesion agent is preferably included in an amount in a range of about 10% to about 90% by weight of the treatment composition (exclusive of any bound water or other solvent), more preferably in a range of about 20% to about 80% by weight of the treatment composition, and most preferably in a range of about 40% to about 75% by weight of the treatment composition.

Examples of active agents include dental bleaching agents, desensitizing agents, remineralizing agents, antimicrobial agents, anti-plaque agents, anti-tartar agents, mouth freshening agents, and medicaments.

The dental treatment composition may include other components as desired, including but not limited to, plasticizers, humectants, solvents, bleaching agent stabilizers, bleaching agent activators, neutralizing agents, particulate thickening agents, flavorants, sweeteners, and the like.

Reference is now made to the drawings, which illustrate exemplary dental treatment trays according to the invention that were manufactured by injection molding so as to have a thickness less than about 0.015 inch. It should be understood that the following dental trays are merely illustrative and not limiting as to shape, size, etc. FIG. 1 is a perspective view of an exemplary dental treatment tray 100 comprising a shaped tray body 102 injection molded from a thermoplastic composition comprising one or more thermoplastic polymers and one or more plasticizers. The shaped tray body 102 further includes a front side wall 104, a rear side wall 106, and a bottom wall 108 bridging the front side wall 104 and rear side wall 106. The front side wall 104, rear side wall 106, and bottom wall 108 together form a shaped tray body 102 having an approximate U-shaped cross section and a generally horseshoe-shaped curvature.

The size, shape and curvature of the shaped tray body 102 are advantageously selected in order for the horseshoe-shaped curvature to generally approximate the curvature of a person's dental arch. The U-shaped cross section generally corresponds to and defines an interior cavity of the tray body 102. The depth of the interior cavity of the tray body 102 is selected in order for the front and rear side walls 104, 106 to extend over a desired portion of a person's teeth, and optionally, over a portion of the person's gums. Because of the flexibility of the shaped tray body 102 and the ability of the front side wall 104, rear side wall 106, and bottom wall 108 to conform to a person's teeth, a generically sized and shaped dental tray 100 can accommodate significant variations in the size and shape of people's dental arches. Nevertheless, it is within the scope of the invention to provide dental trays 100 that are sized and configured to correspond to either a person's upper or lower teeth (the lower dental arch typically being smaller than the upper arch, with lower teeth that are typically smaller than the upper teeth). It is also within the scope of the invention to provide varying-sized treatment trays to account for variability among different people's dental arches and/or teeth (e.g., adults versus children, large mouths versus small mouths, large teeth versus small teeth).

Figure 2A:
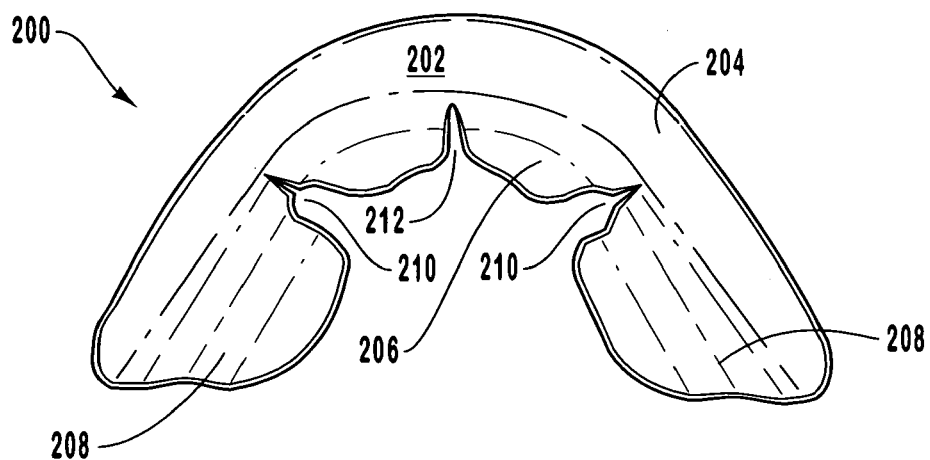
FIG. 2A is a perspective view of an exemplary dental treatment tray having anatomical features that help improve fit between the tray and a person's teeth.

FIG. 2A illustrates an alternative embodiment of a dental treatment tray 200 according to the invention that is equipped with anatomical features that allow the dental treatment tray 200 to more closely conform to a person's teeth during use. Dental treatment tray 200 includes a shaped tray body 202 injection molded from a thermoplastic composition comprising one or more thermoplastic polymers and one or more plasticizers. The shaped tray body 202 further includes a front side wall 204 and a bottom wall 206 extending laterally relative to the front side wall 204. Aside from the anatomical features discussed more fully below, the front side wall 204 and bottom wall 206 together form a tray body 202 having an approximate L-shaped cross section and a generally horseshoe-shaped curvature. Owing to the flexibility of tray body 202, a portion of the bottom wall 206 is able to curve up and around the lingual tooth surfaces so as to form a rear side wall during use.

The tray body 202 further includes various anatomical features that help the tray 200 better conform to the natural features of a person's teeth. One such feature is a pair of V-shaped sections 208, each located on either side of the bottom wall 206 in the region of a person's molars. The V-shaped sections 208 better adapt to depressions typically found in the top surfaces of a person's molars, thereby better conforming to the natural contours of the person's molars and preventing the bottom wall 206 from essentially spanning the molar depressions like a bridge. Because the V-shaped sections 208 better conform to the contours of a person's molars, the inevitable clenching of a person's teeth during a dental treatment is less likely to tug on and displace the front and/or rear side walls of the tray (i.e., if the bottom wall 206 were otherwise pushed into the depressions found in the molars, effectively shortening the length of the bottom wall 206 and tugging on and pulling down the front and/or rear side walls from the tooth surfaces).

Another anatomical feature includes a plurality of side cuts 210 positioned so as to help the bottom wall 206 better conform to abrupt changes in the diameters of a person's teeth as the bottom wall is curved so as to cover the lingual surfaces of a person's teeth, particularly where the bicuspids and canines meet. The side cuts 210 help to compensate for the fact that bicuspids are significantly thicker than canines by allowing for an abrupt discontinuity in the bottom wall 206 of the dental tray 200. Without these cuts the bicuspids adjacent to the canines would tend to push the bottom wall 206 away from the canines, thus potentially dislodging the bottom wall 206 in this region. These and any other cuts within the bottom wall 206 also help compensate for differences between the inner and outer radii of the dental arch generally defined by the inner and outer tooth surfaces. The side cuts 210 may extend the full width of the bottom wall 206.

In the illustrated embodiment, the side cuts 210 flare open toward an edge of bottom wall 206. This allows the bottom wall 206 to more freely spread open or compress without catching or overlapping other portions of the bottom wall 206. The corners of the bottom wall 206 surrounding the side cutes 210 are preferably rounded so as to provide a more comfortable fit and help prevent inadvertent or nervous catching of the bottom wall 206 by a person's tongue during use.

The bottom wall 206 further includes a front notch 212 near the center of the bottom wall 206. The front notch 212 allows the bottom wall 206 of the dental treatment tray 200 to more easily spread open or compress in the area of the incisors. This is helpful in allowing the bottom wall 206 to more easily conform to differently-sized dental arches. As illustrated, front notch 212 may also have rounded corners.

Figure 2B:
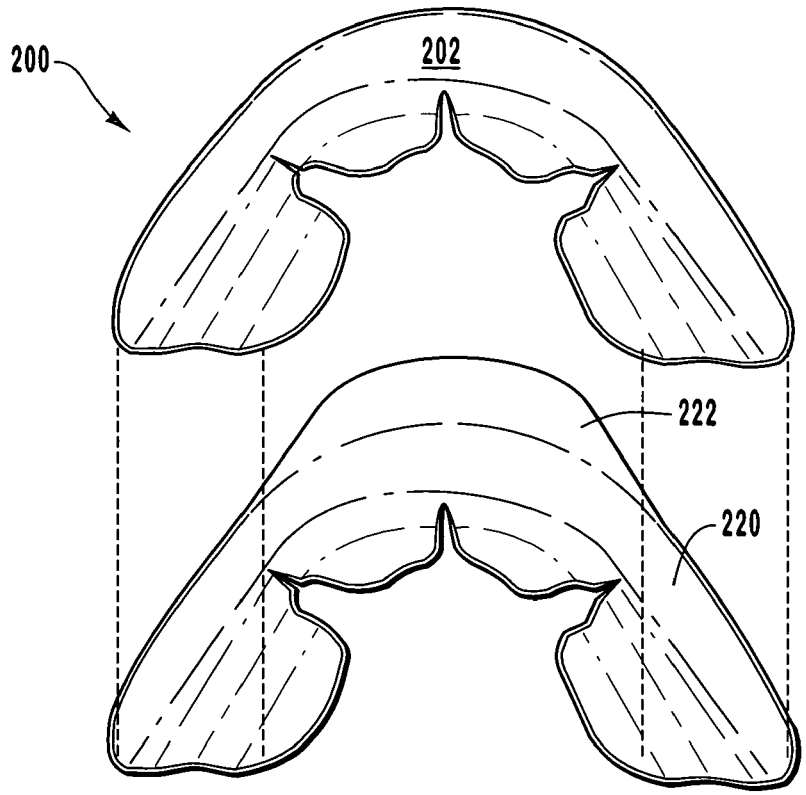
FIG. 2B is an exploded view of the dental treatment tray of FIG. 2A and a complementary outer support tray.
Figure 2C:
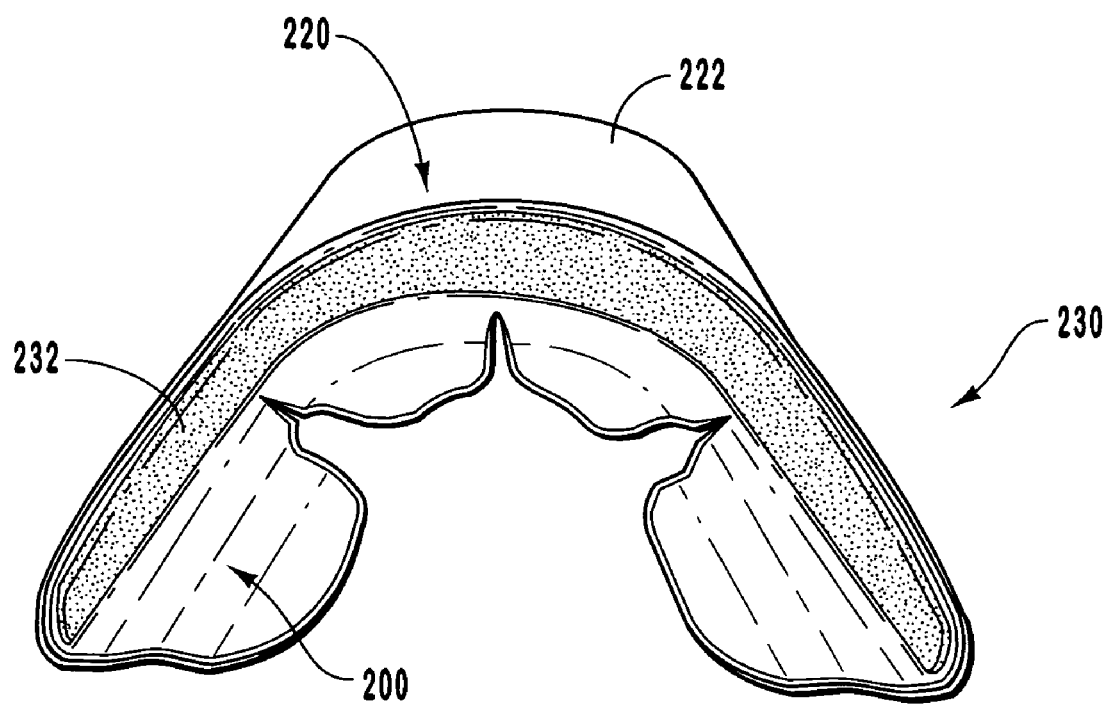
FIG. 2C is a perspective view showing the dental treatment tray of FIGS. 2A and 2B nested within the outer support tray of FIG. 2B, and a treatment composition within the treatment tray.

FIG. 2B is an exploded view showing the dental treatment tray 200 of FIG. 2A in combination with a corresponding outer support tray 220 that is complementary-shaped so as to be capable of receiving the dental treatment tray 200 in a nested configuration (see FIG. 2C). The outer support tray 220 may include the same anatomical features of the dental treatment tray 200 in order to provide a closer fit. The outer support tray 220 advantageously includes a handle 222 extending therefrom in order to facilitate gripping by the user during placement of the dental treatment tray 200 over the person's teeth.

FIG. 2C shows a dental tray assembly 230 comprising the dental treatment tray 200 nested within the outer support tray 220. The handle 222 extends beyond the front side wall of dental treatment tray 200 in order to facilitate removal of the outer support tray 220 after placement of the treatment tray 200 over the person's teeth.

Figure 3:
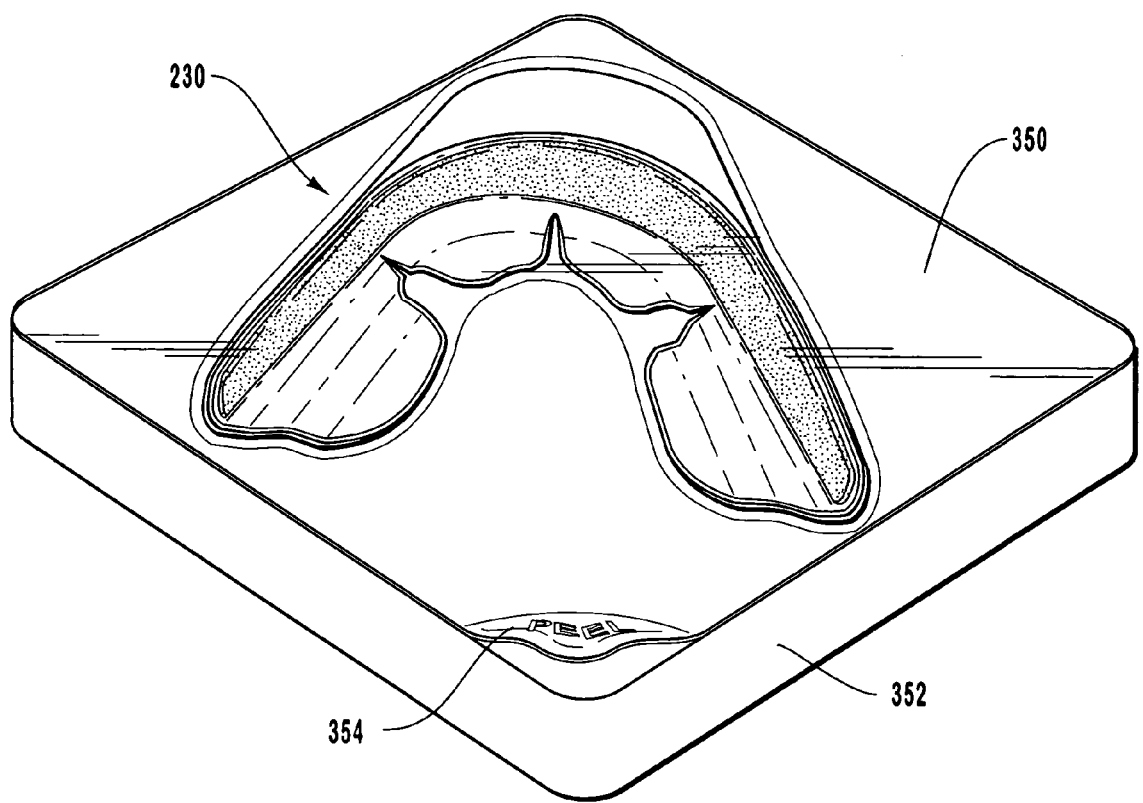
FIG. 3 illustrates an exemplary dental treatment tray and associated outer support tray contained within a sealed protective package having a peelable cover.

In order to protect a dental treatment tray and, optionally a treatment composition pre-loaded therein, from contaminants during storage and prior to use, the dental treatment tray can be packaged within a sealed container or package. FIG. 3 shows a tray assembly 230 having a treatment composition pre-loaded therein sealed within a protective package 350 that includes a rigid support package 352 and a peelable cover 354. When it is desired to use the tray assembly 230, the peelable cover 354 is removed, exposing the tray assembly 230, which can then be separated from the support package 352. The tray assembly 230 may optionally include a removable protective layer (not shown) placed adjacent to the treatment composition for additional protection.

The dental treatment trays according to the invention can be manufactured using known methods. These include vacuum forming the treatment tray from a sheet of plasticized polymer using a generic model of a dental arch. However, the treatment trays are preferably injection molded into a mold cavity using known techniques. The molten thermoplastic resin has an increased melt flow index as a result of including one or more plasticizers in order to better fill the entire mold cavity, notwithstanding the narrowness of the mold cavity and the close proximity between the mold cavity walls. The plasticized thermoplastic resin is heated to a temperature appropriate for a given thermoplastic resin or blend, injected into the mold cavity, and then allowed to cool to form a solidified dental tray. When the molded dental has cooled sufficiently so as to be form stable, it is removed from the mold.

The dental treatment tray may optionally be nested within an outer support tray and/or pre-filled with a dental treatment composition. Alternatively, a dental tray according to the invention may be provided separately from a dental treatment composition, which is introduced into the tray by the user prior to use. For convenience, one or more dental treatment trays, or tray assemblies comprising treatment trays nested within outer support trays, may be provided in a kit along with one or more dental treatment compositions.

The dental treatment trays according to the invention can be designed to be worn for any desired time period. Due to the extremely comfortable fit between the inventive dental treatment trays and the person's teeth, it is possible to wear such trays for extended periods of time as desired. The dental treatment trays can be worn for as little as a few minutes or as long as several hours. By way of example, not limitation, a typical treatment session of fast duration may last from about 10 to about 30 minutes; a treatment session of intermediate duration may last from about 30 minutes to about 2 hours; and a treatment session of long duration, including professional or overnight treatment while a person is sleeping, may last from about 2 hours to about 12 hours.

When used in combination with a sticky treatment composition, dental treatment trays may possibly be worn while performing normal daily activities, such as talking, drinking, smoking, coughing, smiling, frowning, grimacing, or while sleeping. This greatly decreases their intrusiveness into everyday activities compared to conventional bleaching strips, which do not reliably adhere to teeth, or intrusive bleaching devices such as large, bulky bleaching dental appliances.

Dental treatment trays according to the invention may be worn over a person's upper dental arch, lower dental arch, or both simultaneously. The ability to reliably and comfortably wear dental treatment trays over the upper and lower dental arches simultaneously is another departure from bleaching strips, which are not recommended for use in treating the upper and lower dental arches at the same time.

Figure 4A:
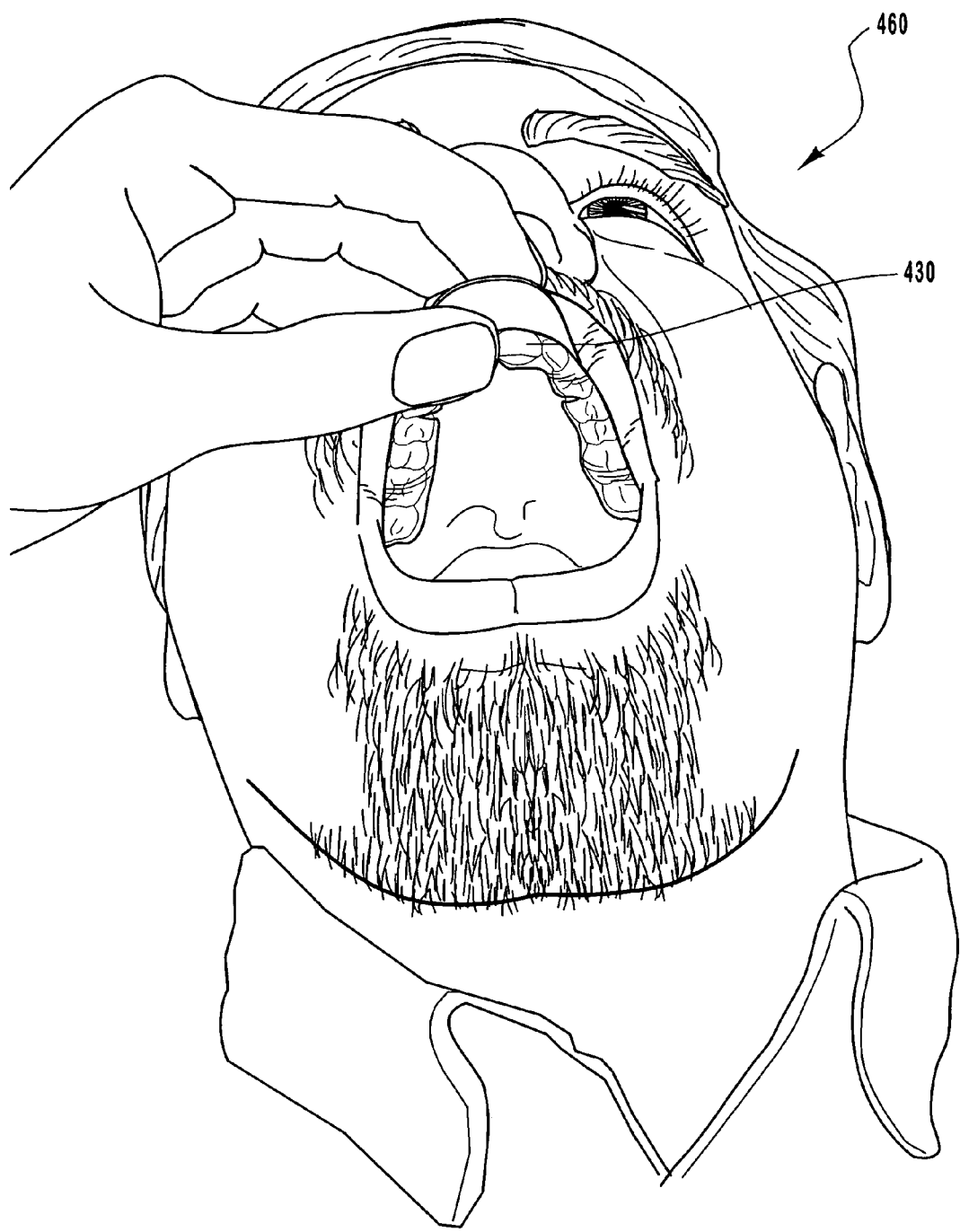
FIG. 4A illustrates a person placing a dental treatment tray according to the invention over the person's upper dental arch.
Figure 4B:
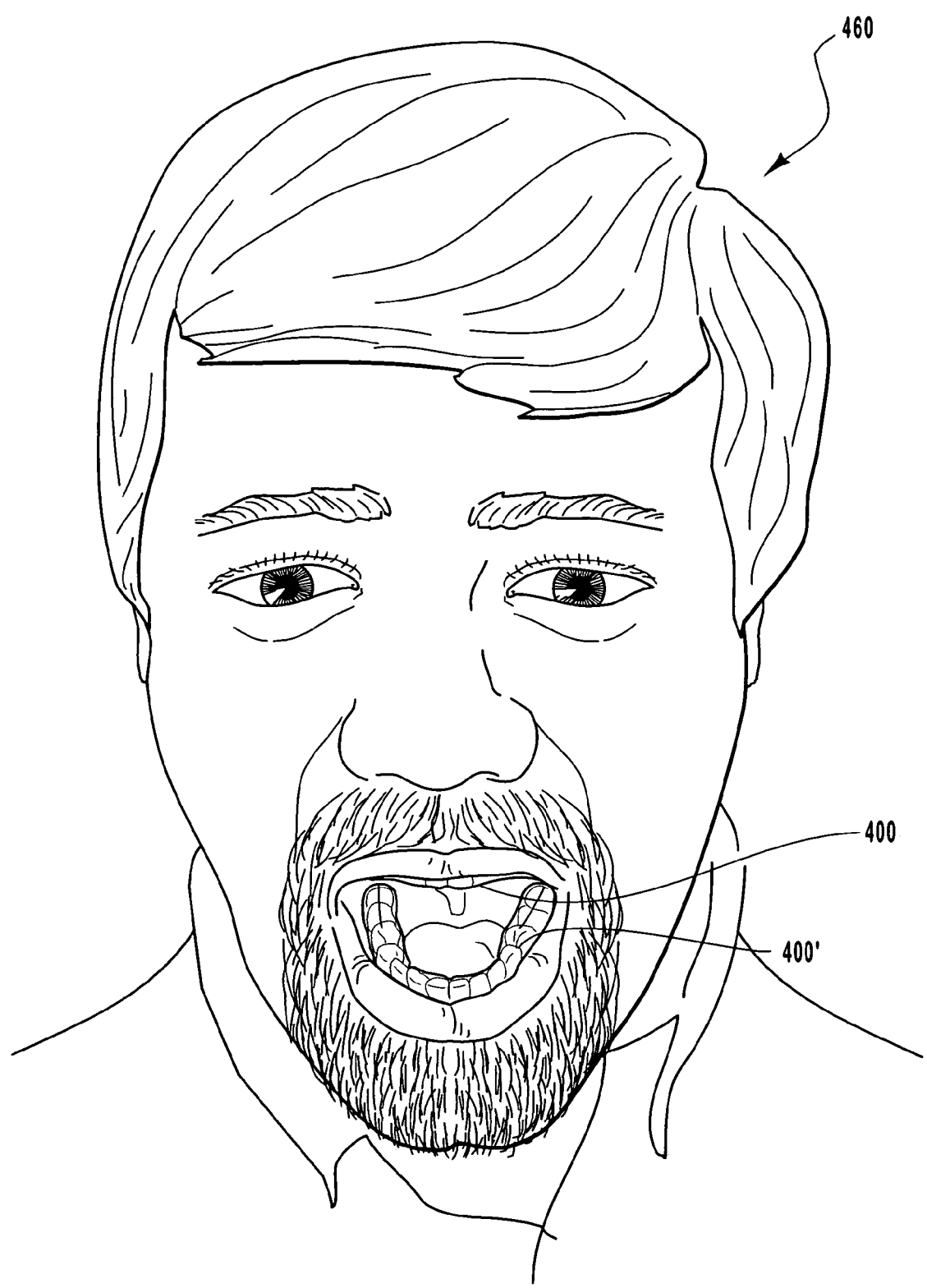
FIG. 4B illustrates dental treatment trays according to the invention in place over both the upper and lower dental arches.

FIG. 4A illustrates a person 460 placing a dental treatment assembly 430 over the person's upper dental arch using an outer support tray to help place an inner treatment tray over the teeth. FIG. 4B illustrates a dental treatment tray 400 in place over the person's upper dental arch and a dental treatment tray 400' over the lower dental arch, both outer support trays having been removed.

To remove the dental treatment tray after a desired time period, the user simply grasps a corner or portion of the tray and pulls it off the teeth. Any residual treatment composition that remains adhered to the person's teeth can be removed by washing or flushing with water and/or by brushing.

EXAMPLES OF THE PREFERRED EMBODIMENTS

Following are examples pf plasticized thermoplastic resins that were used to manufacture dental treatment trays according to the invention by injection molding. The exemplary formulations and manufacturing conditions are given by way of example, and not by limitation. Unless otherwise indicated, all percentages are by weight.

Example 1

A composition for injection molding a dental treatment tray was formed from the following components:

| | |
|---|---|
| DuPont-Dow Engage 8401 | 50% |
| DuPont Elvax 750 | 25% |
| White Mineral Oil | 25% |

Equal weights of DuPont-Dow Engage 8401 and white mineral oil were compounded at a temperature between about 150° F. and about 400° F. for a thorough and even dispersion to create an Engage 8401/white mineral oil mixture. Equal weights of DuPont-Dow Engage 8401 and DuPont Elvax 750 pellets were dry mixed at room temperature until the pellets were evenly dispersed to create an Engage 8401/Elvax 750 mixture. Equal weights of the Engage 8401/white mineral oil mixture and the Engage 8401/Elvax 750 mixture were then mixed together at a temperature between about 200° F. and about 400° F. to form an even dispersion and yield a thermoplastic melt comprising the thermoplastic resins and plasticizer. Dental trays according to the invention were formed by injection molding the thermoplastic melt into a mold cavity, cooling the molded tray material, and then removing the solidified tray once cooled sufficiently so as to be form stable. The injection molded dental trays had a thickness of about 0.008 inch.

Example 2

A composition for injection molding a dental treatment tray was formed from the following components:

| | |
|---|---|
| DuPont-Dow Engage 8401 | 20% |
| DuPont Elvax 750 | 40% |
| White Mineral Oil | 40% |

The components were mixed together in a manner so as to form a thermoplastic melt comprising the thermoplastic resins and plasticizer. Various dental trays were injection molded from the thermoplastic melt to yield trays having thicknesses of about 0.006 inch, about 0.008 inch, and about 0.010 inch.

Example 3

A composition for injection molding a dental treatment tray was formed from the following components:

| | |
|---|---|
| DuPont-Dow Engage 8401 | 80% |
| DuPont Elvax 750 | 10% |
| White Mineral Oil | 10% |

The components were mixed together in a manner so as to form a thermoplastic melt comprising the thermoplastic resins and plasticizer. Various dental trays were injection molded from the thermoplastic melt to yield trays having thicknesses of about 0.008 inch and about 0.010 inch.

Example 4

A composition for injection molding a dental treatment tray was formed from the following components:

| | |
|---|---|
| DuPont-Dow Engage 8401 | 55% |
| Paraffin Wax | 15% |
| White Mineral Oil | 30% |

The components were mixed together in a manner so as to form a thermoplastic melt comprising the thermoplastic resins and plasticizer. Shaped dental trays were injection molded from the thermoplastic melt to yield trays having thicknesses of about 0.006 inch.

Example 5

A composition for injection molding a dental treatment tray was formed from the following components:

| | |
|---|---|
| DuPont-Dow Engage 8401 | 45% |
| Paraffin Wax | 5% |
| White Mineral Oil | 50% |

The components were mixed together in a manner so as to form a thermoplastic melt comprising the thermoplastic resins and plasticizer. Various dental trays were injection molded from the thermoplastic melt to yield trays having thicknesses of about 0.006 inch, about 0.008 inch, and about 0.010 inch.

Example 6

A hypothetical composition for injection molding a dental treatment tray is formed from the following components:

| | |
|---|---|
| DuPont-Dow Engage 8401 | 70% |
| Paraffin Wax | 20% |
| White Mineral Oil | 10% |

The components are mixed together in a manner so as to form a thermoplastic melt comprising the thermoplastic resins and plasticizer. Shaped dental trays are injection molded from the thermoplastic melt to yield trays having thicknesses less than about 0.015 inch.

Following are examples of exemplary dental treatment compositions that can be used in combination with dental treatment trays of the invention.

Example 7

An initially flowable composition suitable for use in manufacturing a substantially solid treatment composition was formed by mixing together the following components:

| | |
|---|---|
| Ethanol | 31.95% |
| Water | 10% |
| Polyvinyl Pyrrolidone (M.W. = 1.3 million) | 27% |
| Polyvinyl Pyrrolidone (M.W. of about 60,000) | 10% |
| Sodium Laurel Sulfate | 0.5% |
| Glycerine | 15% |
| Sucralose 25% solution | 0.5% |
| Peach Flavor | 4% |
| Potassium Nitrate | 0.8% |
| Sodium Fluoride | 0.25% |

The resulting composition is spread over the surface of a dental tray and then dried so as to form a substantially solid treatment composition. The treatment composition is initially dry to the touch, but became very sticky when contacted with water or saliva during use. The potassium nitrate provides a dental desensitizing effect. The sodium fluoride provides both a desensitizing and remineralizing effect.

Example 8

A sticky, viscous dental bleaching composition was prepared by mixing together the following components:

| | |
|---|---|
| Water | 22.5% |
| EDTA Disodium | 0.1% |
| Carbamide Peroxide | 18.5% |
| Sucralose 25% solution | 0.75% |
| Glycerine | 41.6% |
| Carbopol 974 | 5.3% |
| Sodium Hydroxide 50% solution | 2.25% |
| Polyvinyl Pyrrolidone (M.W. = 1.3 million) | 2% |
| Carboxymethyl Cellulose | 4% |
| Watermelon Flavor | 3% |

A bead of dental bleaching composition is spread along the front side wall of a treatment tray according to the invention. Alternatively, the dental bleaching composition is placed over a substantially solid adhesive composition preloaded within a dental treatment tray.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A thin-walled, flexible dental treatment tray for use in applying a dental treatment composition to a person's teeth and/or gums, the dental treatment tray manufactured according to a process comprising:
    injection molding a thin, flexible tray body from a thermoplastic composition comprising a thermoplastic resin and a plasticizer included in amount so as to render the thermoplastic composition injection moldable at a thickness of about 0.015 inch or less; and
    demolding the injection-molded tray body to yield the thin-walled, flexible dental treatment tray, the injection-molded tray body having a front side wall and a bottom wall extending laterally from the front side wall, the injection-molded tray body having a thickness less than about 0.015 inch.

2. A dental treatment tray as recited in claim 1, wherein the plasticizer comprises at least one plasticizer that is a liquid at room temperature.

3. A dental treatment tray as recited in claim 1, wherein the plasticizer comprises at least one plasticizer that is a solid at room temperature.

4. A dental treatment tray as recited in claim 1, wherein the plasticizer comprises at least one member selected from the group consisting of oils, mineral oil, white mineral oil, paraffin oil, waxes, paraffin wax, petrolatum, liquid petrolatum, and nujol.

5. A dental treatment tray as recited in claim 1, wherein the plasticizer is included in an amount in a range of 1% to about 90% by weight of the tray body.

6. A dental treatment tray as recited in claim 1, wherein the plasticizer is included in an amount in a range of 5% to about 75% by weight of the tray body.

7. A dental treatment tray as recited in claim 1, wherein the plasticizer is included in an amount in a range of 10% to about 60% by weight of the tray body.

8. A dental treatment tray as recited in claim 1, wherein the plasticizer is included in an amount in a range of 20% to about 50% by weight of the tray body.

9. A dental treatment tray as recited in claim 1, wherein the thermoplastic material comprises at least one member selected from the group consisting of polyolefins, ethylene-vinyl acetate copolymer, ethylene-vinyl alcohol copolymer, polycaprolactone, polyvinyl chloride, polyesters, polycarbonates, polyamides, polyurethanes, and polyesteramides.

10. A dental treatment tray as recited in claim 1, wherein the thermoplastic resin is included in an amount in a range of 10% to about 99% by weight of the tray body.

11. A dental treatment tray as recited in claim 1, wherein the thermoplastic resin is included in an amount in a range of 25% to about 95% by weight of the tray body.

12. A dental treatment tray as recited in claim 1, wherein the thermoplastic resin is included in an amount in a range of 40% to about 90% by weight of the tray body.

13. A dental treatment tray as recited in claim 1, wherein the thermoplastic resin is included in an amount in a range of 50% to about 80% by weight of the tray body.

14. A dental treatment tray as recited in claim 1, wherein the thermoplastic material comprises a mixture of ethylene-vinyl acetate copolymer and ethylene-octene copolymer.

15. A dental treatment tray as recited in claim 14, wherein the ratio of the ethylene-octene copolymer to the ethylene-vinyl acetate copolymer is in a range of about 1:20 to about 20:1.

16. A dental treatment tray as recited in claim 14, wherein the ratio of the ethylene-octene copolymer to the ethylene-vinyl acetate copolymer is in a range of about 1:10 to about 10:1.

17. A dental treatment tray as recited in claim 14, wherein the ratio of the ethylene-octene copolymer to the ethylene-vinyl acetate copolymer is in a range of about 1:5 to about 5:1.

18. A dental treatment tray as recited in claim 1, the tray body having a thickness less than about 0.010 inch.

19. A dental treatment tray as recited in claim 1, the tray body having a thickness less than about 0.005 inch.

20. A dental treatment tray as recited in claim 1, the tray body having an approximate L-shaped cross section.

21. A dental treatment tray as recited in claim 1, the tray body further comprising a rear side wall extending laterally from the bottom wall, the tray body having an approximate U-shaped cross section.

22. A dental treatment assembly comprising the dental treatment tray of claim 1 and a complementary-shaped outer support tray configured to receive the dental treatment tray in a nested configuration.

23. A dental treatment assembly as recited in claim 22, the outer support tray further including a handle that extends beyond the front side wall of the dental treatment tray when the treatment tray and support tray are nested together.

24. A dental treatment assembly as recited in claim 22, the dental treatment assembly being contained within a sealed packaging container.

25. A dental treatment assembly as recited in claim 24, further comprising a dental treatment composition preloaded within the dental treatment tray.

26. A kit comprising at least one dental treatment tray according to claim 1 and at least one dental treatment composition.

27. A thin-walled, flexible dental treatment tray for use in applying a dental treatment composition to a person's teeth and/or gums, the dental treatment tray manufactured according to a process comprising:

injection molding a thin, flexible the tray body from a composition comprising:

about 25% to about 95% by weight of a thermoplastic resin; and about 5% to about 75% by weight of a plasticizer so as to render the thermoplastic composition injection moldable at a thicknesses of about 0.015 inch or less; and demolding the injection-molded tray body to yield the thin-walled, flexible dental treatment tray, the injection-molded tray body having a front side wall, a bottom wall extending laterally from the front side wall, and a thickness less than about 0.015 inch.

28. A thin-walled, flexible dental treatment tray for use in applying a dental treatment composition to a person's teeth and/or gums, the dental treatment tray manufactured according to a process comprising:

injection molding a thin, flexible tray body from a composition comprising a thermoplastic resin and a plasticizer, the thermoplastic resin comprising ethylene-octene copolymer and ethylene vinyl acetate copolymer, the plasticizer being included in amount so as to render the thermoplastic composition injection moldable at a thickness of about 0.015 inch or less; and demolding the injection-molded tray body to yield the thin-walled, flexible dental treatment tray, the injection molded tray body having a front side wall, a bottom wall extending laterally from the front side, and a wall thickness less than about 0.015 inch.

* * * * *

UNITED STATES PATENT AND TRADEMARK OFFICE
CERTIFICATE OF CORRECTION

PATENT NO.        : 7,137,814 B2  
APPLICATION NO.   : 10/962,884  
DATED             : November 21, 2006  
INVENTOR(S)       : Fischer et al.

Page 1 of 1

It is certified that error appears in the above-identified patent and that said Letters Patent is hereby corrected as shown below:

Column 8  
Line 31, change "cutes" to --cuts--

Column 14  
Line 31, after "flexible" remove "the"

Signed and Sealed this

Twenty-fifth Day of December, 2007

JON W. DUDAS  
*Director of the United States Patent and Trademark Office*